United States Patent
Iyoshi et al.

(10) Patent No.: US 11,969,149 B2
(45) Date of Patent: Apr. 30, 2024

(54) ENDOSCOPE AND INSERTION SECTION OF ENDOSCOPE

(71) Applicant: OLYMPUS CORPORATION, Tokyo (JP)

(72) Inventors: Eita Iyoshi, Hachioji (JP); Yoshimi Konno, Hachioji (JP); Hiroaki Kinoshita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 709 days.

(21) Appl. No.: 17/106,316

(22) Filed: Nov. 30, 2020

(65) Prior Publication Data

US 2021/0093165 A1 Apr. 1, 2021

Related U.S. Application Data

(63) Continuation of application No. PCT/JP2019/006315, filed on Feb. 20, 2019.

(30) Foreign Application Priority Data

May 31, 2018 (JP) .................................. 2018-105110

(51) Int. Cl.
*A61B 1/00* (2006.01)

(52) U.S. Cl.
CPC ...... *A61B 1/00096* (2013.01); *A61B 1/00071* (2013.01)

(58) Field of Classification Search
CPC ............. A61B 1/00071; A61B 1/0008; A61B 1/00096; A61B 1/00163
See application file for complete search history.

(56) References Cited

U.S. PATENT DOCUMENTS

| 2009/0244727 A1 | 10/2009 | Ishii et al. | |
| 2010/0261961 A1* | 10/2010 | Scott | A61B 1/00165 600/111 |
| 2017/0020365 A1* | 1/2017 | Hamazaki | A61B 1/00105 |

FOREIGN PATENT DOCUMENTS

| EP | 2105777 A1 | 9/2009 |
| JP | H09-234183 A | 9/1997 |
| JP | 2001-127239 A | 5/2001 |
| JP | 2006-239185 A | 9/2006 |
| JP | 2008-200158 A | 9/2008 |

(Continued)

OTHER PUBLICATIONS

International Search Report dated Apr. 16, 2019 issued in PCT/JP2019/006315.

*Primary Examiner* — Aaron B Fairchild
(74) *Attorney, Agent, or Firm* — Scully, Scott, Murphy & Presser, P.C.

(57) ABSTRACT

An endoscope includes: a lens barrel having an opening of a through hole on an outer surface of the lens barrel; a lens inserted into the through hole and having a distal end surface which is disposed in a protruding manner from the outer surface; a first resin disposed between a wall surface of the through hole and a side surface of the lens; and a second resin disposed on a surface of the first resin, a portion of the lens barrel around the opening and an entire circumference of an outer peripheral portion of the distal end surface of the lens, the second resin containing rubber and light blocking particles and having an elastic modulus smaller than an elastic modulus of the first resin.

20 Claims, 4 Drawing Sheets

(56) References Cited

FOREIGN PATENT DOCUMENTS

JP    2009-233244 A    10/2009
JP    2013-013712 A    1/2013

* cited by examiner

ENDOSCOPE AND INSERTION SECTION OF ENDOSCOPE

CROSS REFERENCE TO RELATED APPLICATION

This application is a continuation application of PCT/JP2019/006315 filed on Feb. 20, 2019, and claims benefit of Japanese Application No. 2018-105110 filed in Japan on May 31, 2018, the entire contents of which are incorporated herein by this reference.

BACKGROUND OF THE INVENTION

1. Field of the Invention

The present invention relates to an endoscope where an optical member is fixed to a barrel disposed in a distal end portion of an insertion section by a resin, and an insertion section of an endoscope where an optical member is fixed to a barrel disposed in a distal end portion by a resin.

2. Description of the Related Art

Endoscopes have been widely used, in which an elongated insertion section is inserted into the inside of a body of a subject which cannot be observed from the outside to observe the inside of the body by an image pickup unit disposed in the distal end portion, and treatment is performed using a treatment instrument protruded from the distal end portion. Reprocess treatment including cleaning, disinfecting and sterilization is performed on the endoscopes after use, to prevent infection between patients.

In Japanese Patent Application Laid-Open Publication No. 2013-13712, an endoscope is disclosed where a lens 133 of an illumination optical system and a cover glass 135 of an image pickup optical system, that is, optical members are fixed to a distal end 131 of an insertion section by an adhesive agent 137, and a ring-shaped protruding portion 139 is disposed on an outer peripheral edge of the optical members for preventing flare. An epoxy adhesive or a silicone adhesive is used as the adhesive agent 137, and blackened epoxy adhesive is used for forming the protruding portion 139.

SUMMARY OF THE INVENTION

An endoscope of an embodiment includes: a barrel disposed in a distal end portion of an insertion section and having an opening of a through hole on an outer surface of the barrel; an optical member inserted into the through hole and having a distal end surface which is disposed in a protruding manner from the outer surface; a first resin disposed between a wall surface of the through hole and a side surface of the optical member; and a second resin disposed on a surface of the first resin, a portion of the barrel around the opening and an entire circumference of an outer peripheral portion of the distal end surface of the optical member, the second resin containing rubber and light blocking particles and having an elastic modulus smaller than an elastic modulus of the first resin.

An insertion section of an endoscope of an embodiment includes: a barrel disposed in a distal end portion of the insertion section and having an opening of a through hole on an outer surface of the barrel; an optical member inserted into the through hole and having a distal end surface which is disposed in a protruding manner from the outer surface; a first resin disposed between a wall surface of the through hole and a side surface of the optical member; and a second resin disposed on a surface of the first resin, a portion of the barrel around the opening and an entire circumference of an outer peripheral portion of the distal end surface of the optical member, the second resin containing rubber and light blocking particles and having an elastic modulus smaller than an elastic modulus of the first resin.

DETAILED DESCRIPTION OF THE PREFERRED EMBODIMENTS

First Embodiment

Figure 1:
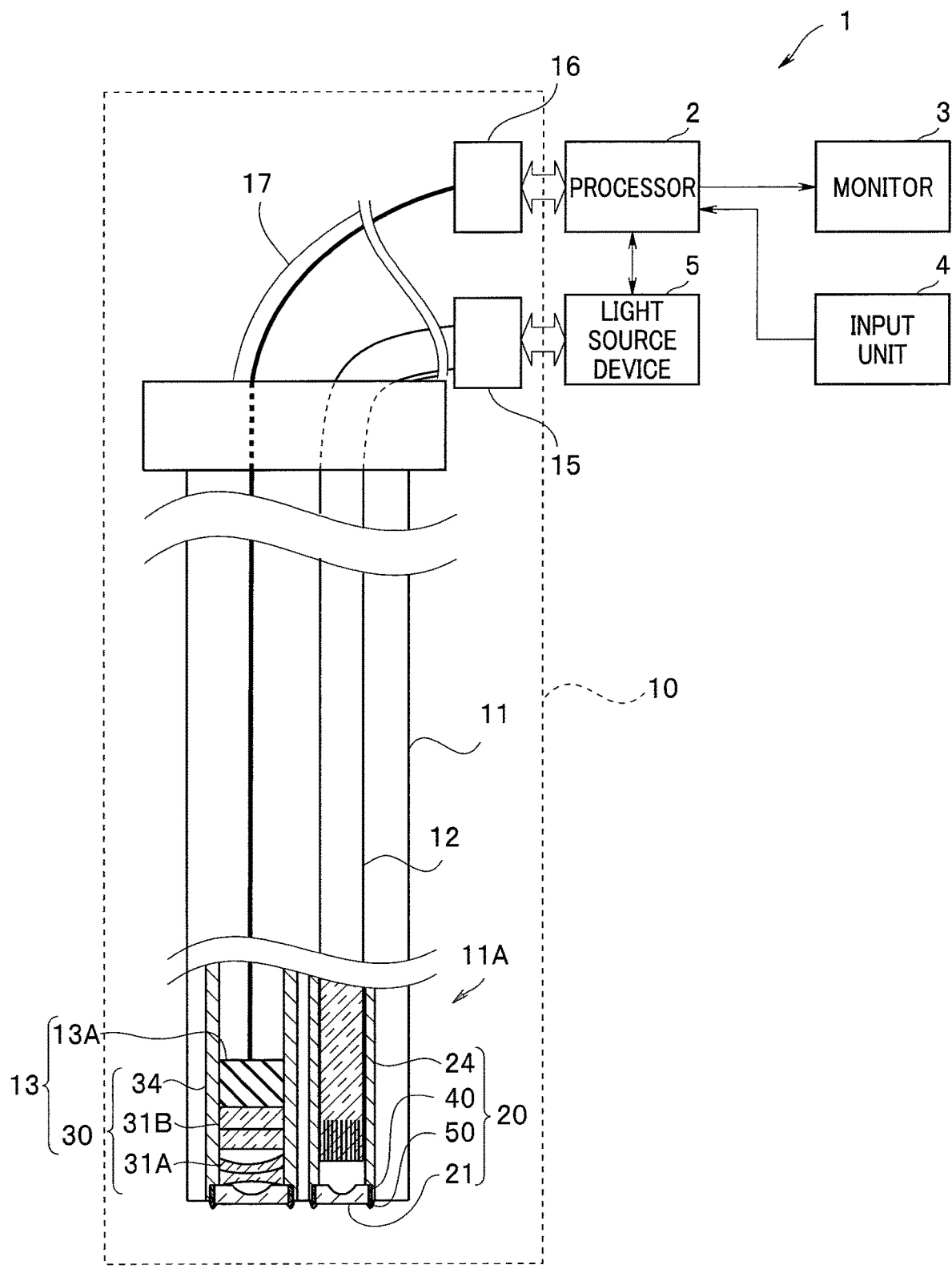
FIG. 1 is a configurational view of an endoscope system including an endoscope of a first embodiment.

As shown in FIG. 1, an endoscope 10 of the present embodiment, together with a processor 2 which processes an image signal, a monitor 3, an input unit 4 for setting a use condition and the like, and a light source device 5, configures an endoscope system 1.

In a description made hereinafter, drawings based on respective embodiments are schematic views. Accordingly, a relationship between a thickness and a width of each component, a ratio between thicknesses, relative angles and the like of the respective components differ from the corresponding relationships of components of an actual endoscope system. There may be a case where the respective components are described with different size relationship or different ratios in each of the drawings. The illustration of some components and the indication of components by symbols may be omitted. In addition a direction of an object direction is defined as a frontward direction.

The endoscope 10 is a so-called flexible endoscope which includes: an elongated flexible insertion section 11 which is inserted into a body; and a universal cord 17 which extends from the insertion section 11 via an operation section (not shown). The insertion section 11 through which a light guide 12 passes includes an image pickup unit 13 in a distal end portion 11A of the insertion section 11. The image pickup unit 13 includes: an image pickup optical unit 30 (hereinafter referred to as "optical unit 30"); and an image pickup device 13A such as a CCD. The universal cord 17 includes, on a proximal end portion side thereof, a light guide connector 15 connected to a light source device 5 and an electronic connector 16 connected to the processor 2.

A light generated by the light source device 5 is guided to the distal end portion 11A via the light guide connector 15 and the light guide 12, and is emitted toward an object as an illumination light by an irradiation optical unit 20 (hereinafter referred to as "optical unit 20"). The illumination light is reflected on a surface of an object, and the reflected light is converged on the image pickup device 13A by the optical unit 30, and is picked up as an image of the object. The image is signal-processed by the processor 2, and the processed image is displayed on a screen of the monitor 3. A wiring board on which an electronic component which applies primary processing to the image pickup signal is disposed may be bonded to the image pickup device 13A.

On the frontmost surface of the distal end portion 11A, a lens 21 which is an optical member of the optical unit 20, and a lens 31 which is an optical member of the optical unit 30 are disposed.

The optical unit 20 includes: the lens 21; and a lens barrel 24 which is a barrel for holding the lens 21. On the other hand, the optical unit 30 includes: lenses 31, 31A, 31B; and a lens barrel 34 which is a barrel for holding the lens 31 and the like.

The types, thicknesses, the number, and a stacking order of the plurality of optical members can be suitably changed. In the endoscope 10, the lens barrel 24 of the optical unit 20 and the lens barrel 34 of the optical unit 30 are provided as separate bodies. However, the lens 21 and the lens 31 may be fixed to a same lens barrel.

The lens 21 and the like are transparent optical members made of glass, quarts, sapphire, stabilized zirconia (YSZ), yttrium-aluminum-garnet (YAG) or the like.

The lens 21 is a planoconcave lens having a negative power for irradiating an illumination light in a wide range. The lens 31 is also a planoconcave lens having a negative power for obtaining a wide field of view. However, the lenses 21, 31 may be a planoconvex lenses depending on the configurations of the optical units 20, 30. Front surfaces of the lenses 21, 31 which form the frontmost surfaces of the optical units 20, 30 may preferably be flat surfaces for prevention of adhesion of a foreign substance and prevention of a damage caused by an impact.

In a case where a cover glass of a parallel flat plate is disposed at the frontmost portion of the optical unit, the optical member which is exposed on the frontmost surface of the distal end portion 11A is not the lens but is the cover glass of the flat plate.

As described later, for example, the lens 21 of the optical unit 20 is fixed to the lens barrel 24 by a first resin 40, and a surface of the first resin 40 is covered by a second resin 50 which forms a ring-shaped protruding portion.

<Configuration of Optical Unit>

Next, the configuration of the optical unit is described by taking the irradiation optical unit 20 as an example.

Figure 2:
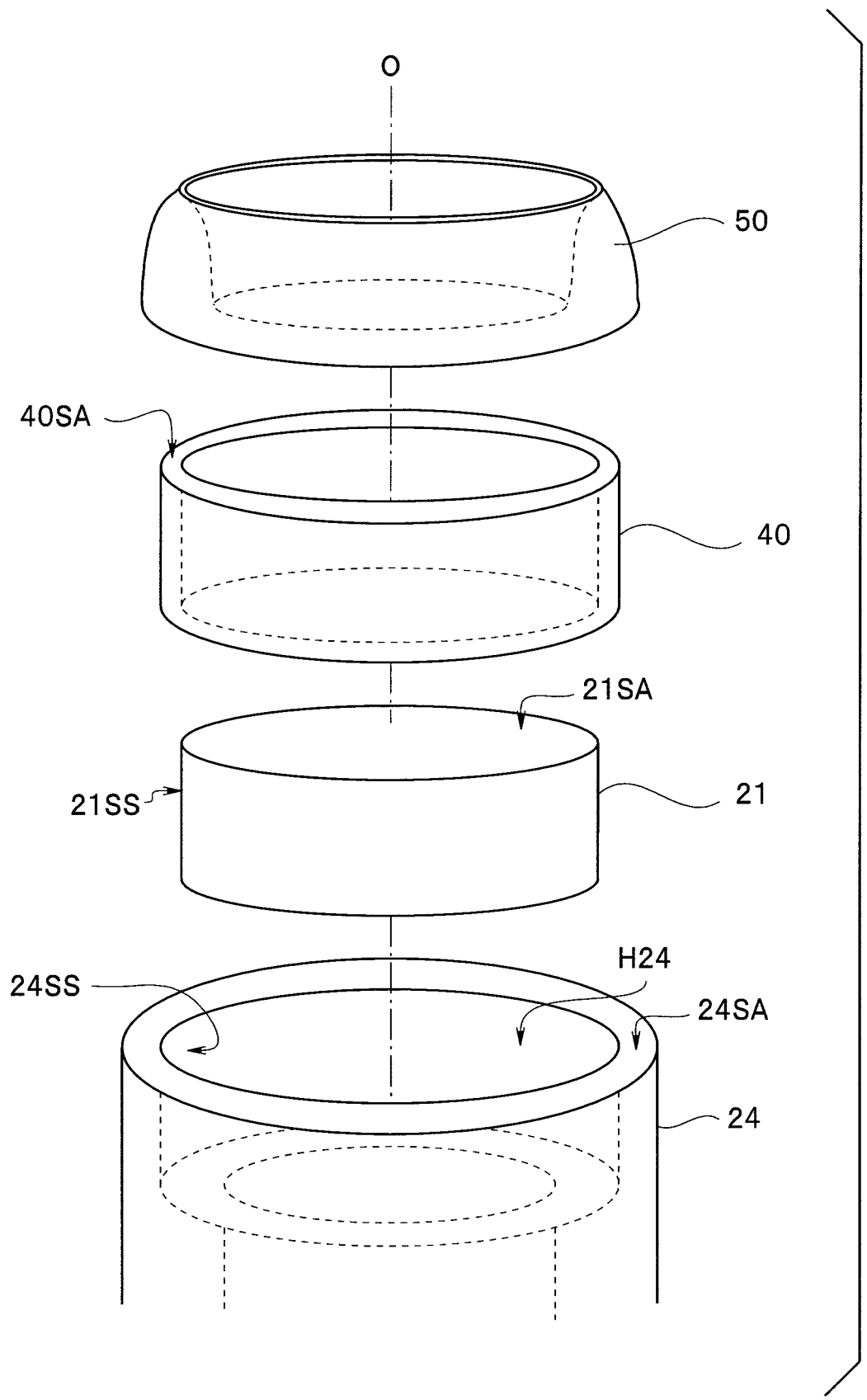
FIG. 2 is a perspective exploded view of an irradiation optical unit of the endoscope of the first embodiment.
Figure 3:
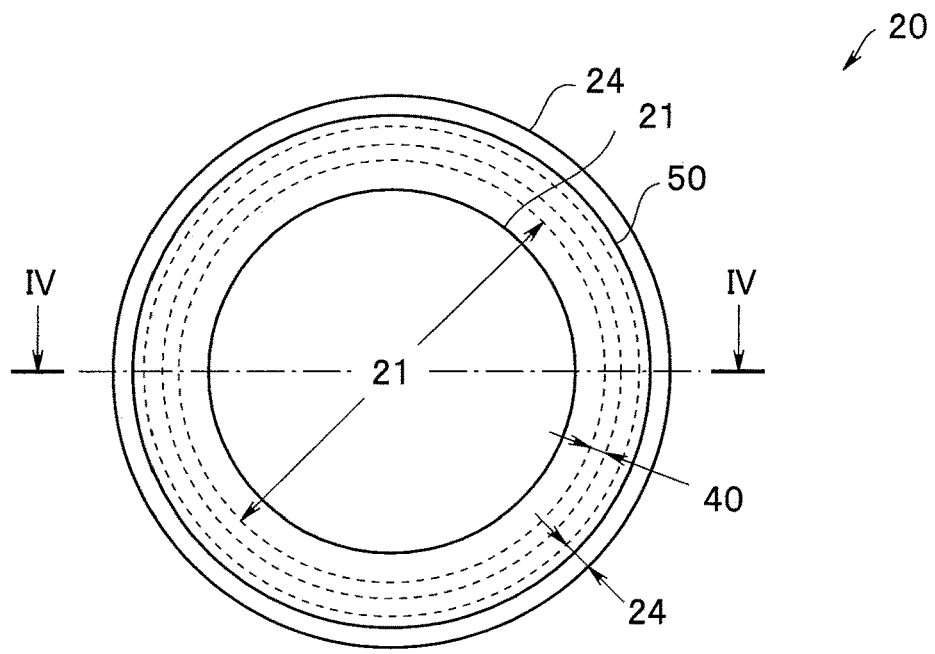
FIG. 3 is a plan view of a frontmost surface of the irradiation optical unit of the endoscope of the first embodiment.
Figure 4:
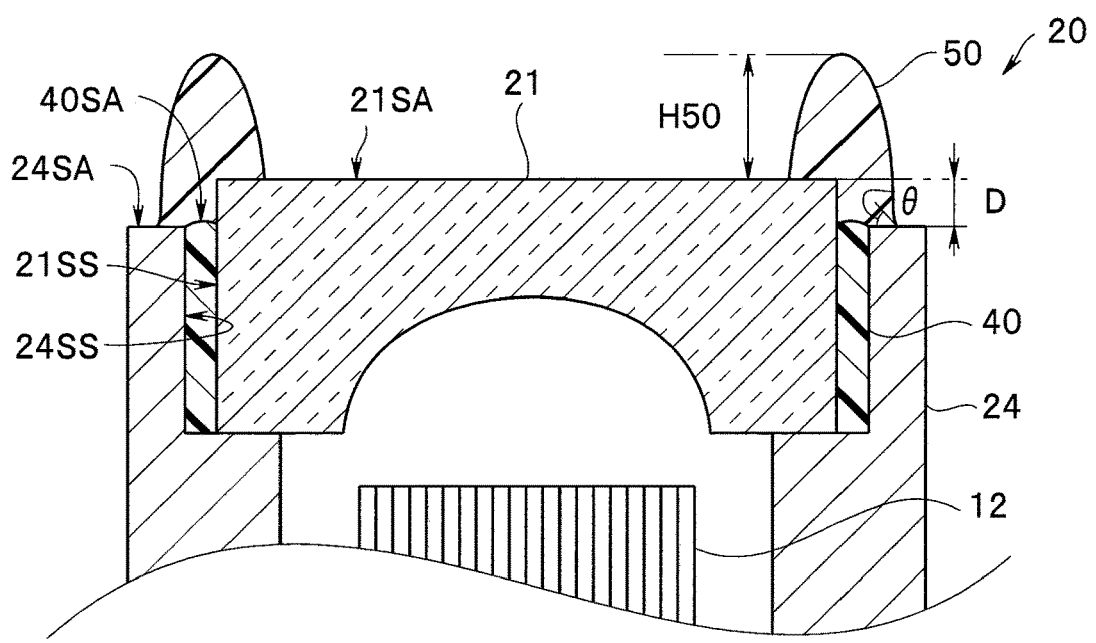
FIG. 4 is a cross-sectional view of the irradiation optical unit of the endoscope of the first embodiment taken along a line IV-IV in FIG. 3.

As shown in FIG. 2 to FIG. 4, the lens barrel 24 of the optical unit 20 is disposed at the distal end portion 11A of the insertion section 11. The lens barrel 24 has an opening of a through hole H24 in an outer surface 24SA. The outer surface 24SA is a front surface which is disposed closest to an object, and exposed to an outside. The lens barrel 24 is made of metal, for example, stainless steel. The lens 21 is inserted into the through hole H24 of the lens barrel 24, and a distal end surface 21SA of the lens 21 is disposed in a protruding manner from the outer surface 24SA of the lens barrel 24.

A protruding amount D of the distal end surface 21SA from the outer surface 24SA may preferably be within a range of 10 µm or more and 150 µm or less. When the protruding amount D is less than the above-described range, or the distal end surface 21SA does not protrude from the outer surface 24SA, a foreign substance is liable to adhere to a stepped portion of an outer periphery of the distal end surface 21SA, and the removal of such a foreign substance is not easy. When the protruding amount D exceeds the above-described range, the second resin 50 described later cannot be easily disposed, and the stepped portion cannot be easily eliminated even when the second resin 50 is disposed.

The first resin 40 is disposed between a wall surface 24SS of the through hole H24 and a side surface 21SS of the lens 21. The first resin 40 is an adhesive agent which fixes the lens 21 to the lens barrel 24.

The optical unit 20 includes the second resin 50 which forms a ring-shaped protruding portion, and covers the surface 40SA of the first resin 40, that is, the outer surface which is not in contact with the wall surface 24SS or the side surface 21SS. In order to completely cover the surface 40SA of the first resin 40, the second resin 50 is disposed also around the opening of the lens barrel 24 and an entire circumference of an outer peripheral portion (outer peripheral edge) of the distal end surface 21SA of the lens 21.

Although the distal end surface 21SA protrudes from the outer surface 24SA, the stepped portion is covered with the second resin 50. Accordingly, the endoscope 10 possesses a favorable optical characteristic, and cleaning and the like of the endoscope 10 can be performed easily.

In the endoscope 10, the first resin 40 is a thermo-setting epoxy resin (elastic modulus: E=5 GPa), and the second resin 50 is a thermo-setting fluororubber containing 5 wt % of carbon black particles (elastic modulus: E=0.012 GPa).

In other words, the second resin 50 has an elastic modulus E smaller than that of the first resin 40. The elastic modulus E is Young's modulus measured by performing a tensile test on a resin having a predetermined shape. More specifically, the elastic modulus E is a tensile elastic modulus measured by a method in accordance with ASTM D882 standard.

The elastic modulus E40 of the first resin 40 may preferably be 1 GPa or more, and more particularly preferably be 2 GPa or more, for example, for firmly fixing the lens 21 to the lens barrel 24. In a case where the elastic modulus E40 is less than the above-mentioned range, there is a concern that an optical characteristic of the lens 21 is deteriorated, when the lens 21 moves in the through hole H24 of the lens barrel 24 due to an external impact on the lens 21. Although an upper limit of the elastic modulus E40 is not particularly limited, the upper limit of the elastic modulus E40 is 10 GPa, for example.

The first resin 40 may preferably be a thermo-setting resin, and may be an epoxy resin (E=5 GPa), a polystyrene resin (E=3 GPa), a melamine resin (E=9 GPa) or the like.

On the other hand, the second resin 50 having a thermo-setting property does not contribute to the positioning of the lens 21, unlike the first resin 40. Accordingly, there arises no problem even when the elastic modulus of the second resin 50 is smaller than the elastic modulus of the first resin 40.

The elastic modulus E50 of the second resin 50 may preferably be 0.1 GPa or less, and more preferably be 0.05 GPa or less, for example. Although the lower limit of the elastic modulus E50 is not particularly limited, the lower limit of the elastic modulus E50 is 0.001 GPa, for example.

When the elastic modulus E50 is within the above-mentioned range or less, the second resin 50 is not likely to be damaged even when the second resin 50 receives an impact. Further, when the elastic modulus E50 is within the above-mentioned range or less, even when a degraded layer is formed on a surface of the second resin 50, a stress generated by the degraded layer is alleviated in the second resin 50 and hence, there is no concern that peeling of an adhering surface occurs.

The elastic modulus E50 of the second resin 50 may preferably be 1/10 or less of the elastic modulus E40 of the first resin 40. By setting the elastic modulus E50 of the second resin 50 to 1/10 or less of the elastic modulus E40 of the first resin 40, fixing of the lens 21 by the first resin 40 can be ensured and hence, the damage of the second resin 50 can be prevented.

A resin having low elasticity may be used as the second resin 50. For example, when a melamine resin is used as the first resin 40, a silicone resin (E=0.06 GPa) having an elastic modulus which is 1/10 or less of an elastic modulus of a melamine resin may be used as the second resin 50. However, when an epoxy resin is used as the first resin 40, rubber (E≤0.05 GPa) which is a resin having a further lower elasticity is used as the second resin 50.

When an epoxy resin is used as the first resin 40, it is preferable to specifically use fluororubber, silicone rubber, acrylic rubber, nitrile rubber, ethylene-propylene rubber or the like, as the second resin 50. In the present invention, "rubber" also includes a resin which contains rubber as a main component and a rubber modified resin, provided that the elastic modulus E50 of such resins is 0.05 GPa or less.

It is preferable that the second resin 50 exhibits more excellent chemical resistance than the first resin 40. Therefore, fluororubber (E=0.012 GPa) is particularly preferable for the second resin 50. Examples of the fluororubber include vinylidene fluoride rubber, tetrafluoroethylene propylene rubber, and tetrafluoroethylene perfluoromethyl vinyl ether rubber which have (CF2) as a basic skeleton.

Although the distal end surface 21SA protrudes from the outer surface 24SA, the stepped portion is covered by the second resin 50. Accordingly, cleaning and the like of the endoscope 10 can be performed easily, and the endoscope 10 possesses a favorable optical characteristic. Further, fixing of the lens 21 is ensured by the first resin 40, and the second resin 50 having a protruding shape is not likely to be damaged. Accordingly, the endoscope 10 has high reliability.

The second resin 50 prevents diffusion of illumination light, and prevents flare which occurs due to incidence of the illumination light into the image pickup optical system. The second resin 50 is a light blocking resin containing light blocking particles, and forms the ring-shaped protruding portion which surrounds the distal end surface 21SA of the lens 21. A protruding amount H50 of the protruding portion from the distal end surface 21SA may preferably be within a range of 1 μm or more and 100 μm or less. When the protruding amount H50 is less than the above-mentioned range, a sufficient flare preventing effect cannot be obtained. On the other hand, when the protruding amount H50 of the protruding portion exceeds the above-mentioned range, an irradiation range of an illumination light is narrowed or the second resin 50 is likely to be easily damaged.

When the second resin 50 contains 0.01 wt % or more and 5 wt % or less of light blocking particles, a light blocking performance of the second resin 50 is ensured. The light blocking particles are made of a material having a lower light transmissivity than that of the second resin 50. The light blocking particles are organic particles, metal particles or inorganic material particles. Two kinds or more of particles made of different materials may be used in combination as the light blocking particles. The shape of the light blocking particle may be a sphere or any shape such as an elliptical body shape, a plate shape or a needle shape. Two kinds or more particles having different shapes may be used in combination as the light blocking particles. Sizes (particle sizes) of the light blocking particles are, for example, 50 nm to 20 μm. The sizes of the light blocking particles may be uniform over the whole second resin 50 or may have variations.

As the light blocking particles, at least one of carbon black or black titanium oxide may be preferably used from a viewpoint of a cost, a light blocking property and dispersion property of the light blocking particles into a resin.

The first resin 40 may also preferably contain light blocking particles for preventing the reflection on the wall surface 24SS of the lens barrel 24. The first light blocking particles contained in the first resin 40 may be the same as or different from the second light blocking particles contained in the second resin 50.

As described previously, it is known that the larger a thickness of a region of the thermo-setting resin is, the larger a shrinkage of the thermo-setting resin at the time of curing is and hence, peeling is liable to occur. The inner peripheral portion of the second resin 50 is disposed on the distal end surface 21SA of the lens 21, while the outer peripheral portion of the second resin 50 is disposed on the outer surface 24SA of the lens barrel 24. The thickness of the outer peripheral portion of the second resin 50 is larger than the thickness of the inner peripheral portion of the lens 21 by the protruding amount D of the distal end surface 21SA. Accordingly, there is a possibility that the outer peripheral portion of the second resin 50 becomes a point from which peeling starts to occur.

Accordingly, as shown in FIG. 4, it is preferable that a contact angle θ of the second resin 50 with respect to the outer surface 24SA of the lens barrel 24 is set to 45 degrees or less.

A light absorbing film, for example, a black chromium plating film may preferably be formed on the wall surface 24SS of the lens barrel 24 for prevention of reflection. In the endoscope 10, a light absorbing film may also preferably be formed on the outer surface 24SA of the lens barrel 24.

When the outer surface 24SA is a mirror surface, it is not easy to set the contact angle θ to 45 degrees or less. However, the light absorbing film such as the black chromium plating film has large surface roughness (Rz) and hence, the contact angle θ of the second resin 50 can be decreased whereby an adhesive strength can be easily enhanced.

Second Embodiment

An endoscope 10A of the second embodiment is similar to the endoscope 10 and hence, components having the same functions are given with the same symbols, and the description of the components is omitted.

Figure 5:
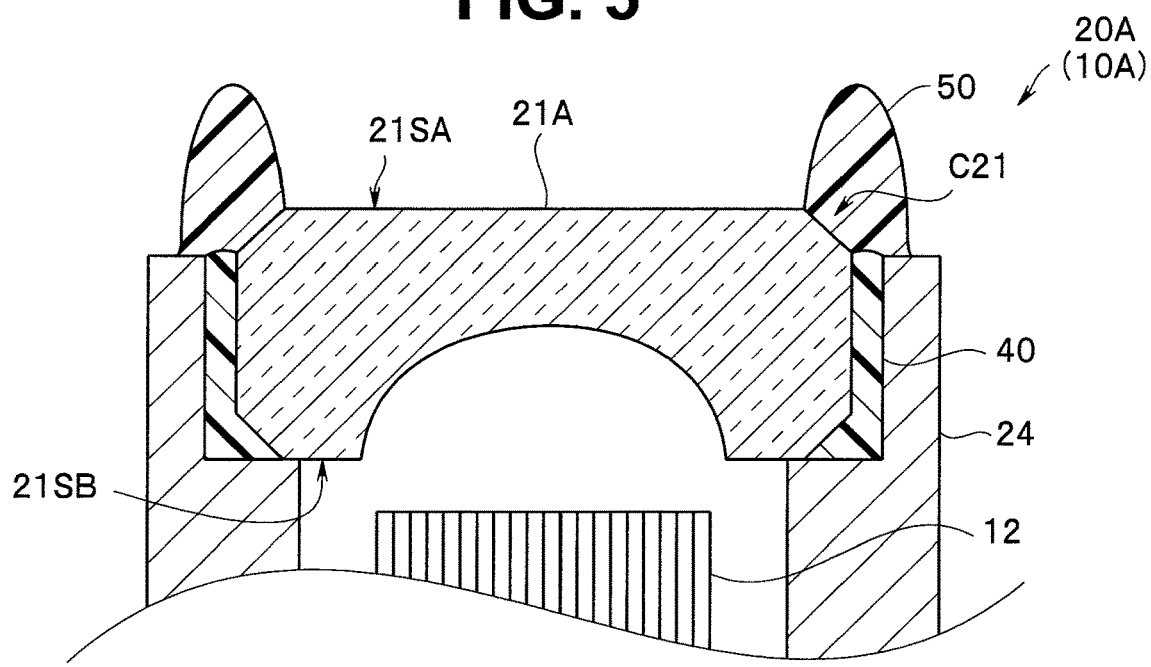
FIG. 5 is a cross-sectional view of an irradiation optical unit of an endoscope of a second embodiment.

As shown in FIG. 5, in a lens 21A of an optical unit 20A of the endoscope 10A, a cutout C21 is formed on an outer peripheral portion of a distal end surface 21SA. In other words, a ridge line where the distal end surface 21SA of the lens 21 and a side surface 21SS of the lens 21 intersect with each other is chamfered.

Chamfering processing is not limited only to processing for cutting out the ridge line into a plane shape, but may be so-called round forming processing for cutting out the ridge line into a curved surface shape. Further, the chamfering processing also includes molding of the ridge line in substantially the same shape as that in the case where the ridge line is processed. A method of processing or molding is not limited to a particular method.

In the lens 21A having the cutout C21, chipping is not likely to occur at the outer peripheral portion of the distal end surface 21SA, even if the lens 21A receives an impact. Note that the lens 21A has a cutout also on a back surface 21SB opposite to the distal end surface 21SA.

In the endoscope 10A, the second resin 50 is not disposed in an optical path region of the distal end surface 21SA, but disposed only in the cutout C21. In other words, the cutout C21 prevents spreading of the second resin 50 to the optical path region of the distal end surface 21SA. Further, the second resin 50 disposed on the cutout C21 exhibits a higher adhering strength than the case where the second resin 50 is disposed on a flat surface and hence, the endoscope 10A has higher reliability than the endoscope 10.

In the optical unit 20A, a non-cutout center of the distal end surface 21SA of the lens 21A protrudes from the outer surface 24SA of the lens barrel by 10 μm or more and 150 μm or less, and the protruding portion of the second resin protrudes from the center of the distal end surface 21SA by 1 μm or more and 100 μm or less.

The endoscope 10A has the advantageous effects of the endoscope 10. Further, in the endoscope 10A, chipping of the lens is not likely to occur, and at the same time, the second resin 50 can be easily disposed on the periphery of the optical path region, and therefore an optical characteristic of the endoscope 10A is more favorable.

Third Embodiment

An endoscope 10B of the third embodiment is similar to the endoscopes 10, 10A and hence, components having the same functions are given with the same symbols, and the description of the components is omitted.

Figure 6:
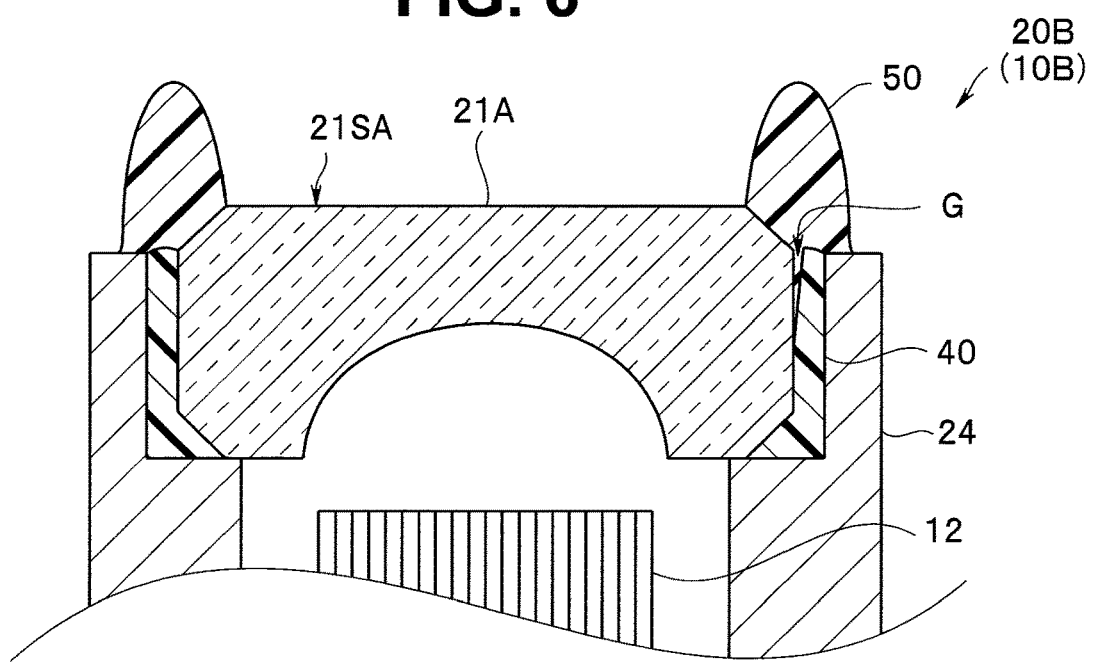
FIG. 6 is a cross-sectional view of an irradiation optical unit of an endoscope of a third embodiment.

As shown in FIG. 6, in an optical unit 20B of the endoscope 10B, a gap G is formed between a first resin 40 and a side surface 21SS of a lens 21. A second resin 50 is also disposed in the gap G.

For example, in the endoscope, there may be a case where the gap G is formed between the first resin 40 and the side surface 21SS of the lens 21 due to an impact or the like during the use of the endoscope and a deterioration with a lapse of time. In other words, there may be a case where peeling occurs on an adhering surface of the first resin 40 having the large Young's modulus. There may be also a case where the second resin 50 covering the first resin 40 is damaged, and as a result, a surface of the first resin 40 is exposed. Still further, as a product specification, some endoscopes do not include the second resin 50.

Even if the gap G partially occurs and a width of the gap G is small such as 1 μm, and the depth of the gap G is shallow, the gap G forms a path through which a moisture invades into the endoscope and hence, which may result in a degradation in the reliability of the endoscope.

The endoscope 10B is manufactured by repairing an endoscope in which the gap G occurs due to deterioration with a lapse of time, for example. In other words, in repairing the endoscope, not only the first resin 40 is filled in the gap G but also the second resin 50 which is a ring-shaped protruding portion is disposed. In such a configuration, the second resin 50 is also disposed in the gap G.

The second resin 50 has an elastic modulus E smaller than that of the first resin 40 and hence, the second resin 50 absorbs an impact from the outside. Further, since the second resin 50 is also disposed in the gap G, an adhesive strength is increased by an anchoring effect. Accordingly, the endoscope 10B has higher reliability than not only the endoscopes 10, 10A but also the endoscope which is repaired by disposing the first resin 40 in the gap G. The second resin 50 disposed in the gap G does not have a large thickness and hence, the influence of the second resin 50 on the positional accuracy of the fixed lens 21 is small.

The endoscope 10B manufactured by repairing the endoscope in which the second resin 50 is not disposed at the time of manufacturing is newly given with a flare preventing effect.

The gap G in which the second resin 50 is disposed may be formed between the first resin 40 and a wall surface 40SS of a through hole H40. Alternatively, the gap G in which the second resin 50 is disposed may be formed between the first resin 40 and a side surface 21SS of a lens 21 and between the first resin 40 and the wall surface 40SS of the through hole H40. In other words, the gap G in which the second resin 50 is disposed may be formed in at least either one of a space between the first resin 40 and the wall surface 40SS of the through hole H40 or a space between the first resin 40 and the side surface 21SS of the lens 21.

In the above-mentioned description, the description has been made by taking the irradiation optical units 20, 20A, 20B, as examples. However, it goes without saying that the image pickup optical unit 30 can have the same advantageous effects as those of the irradiation optical units 20, 20A, 20B by having the same configurations as the irradiation optical units 20, 20A, 20B.

Only the image pickup optical unit 30 of the endoscope may have the above-mentioned configuration. In other words, it is sufficient that the optical member (lens) of the endoscope is the distal end member of at least one of the irradiation optical unit 20 or the image pickup optical unit 30. Further, the plurality of irradiation optical units 20 or the plurality of image pickup optical units 30 may be disposed on the distal end portion 11A.

The description has been made by taking flexible endoscopes 10, 10A, 10B for medical use as examples. However, the endoscopes of the embodiments of the present invention may be endoscopes for industrial use, may be rigid endoscopes, and may be wireless endoscopes having no universal cords.

The present invention is not limited to the above-mentioned embodiments and the like, and various changes, combinations, variations and the like can be made without departing from the gist of the present invention.

What is claimed is:

1. An endoscope comprising:
   an insertion section;
   a barrel disposed in a distal end portion of the insertion section, the barrel comprising:
      a through hole disposed in the barrel, the through hole including an inner wall surface; and
      an opening disposed at a distal end of the through hole;
   an optical member disposed in the through hole, the optical member including a proximal end surface, a side wall surface and a first transitional surface, the first transitional surface being disposed between the proximal end surface and the side wall surface;
   a first resin disposed between the inner wall surface and the side surface; and
   a second resin in contact with each of the first resin, a portion of the barrel and a portion of the optical member, the second resin containing light blocking particles.

2. The endo scope according to claim 1, wherein the optical member further includes a distal end surface and a second transitional surface, the second transitional surface being disposed between the side wall surface and the distal end surface; and
   the first resin having a first elastic modulus, the second resin having a second elastic modulus, and the second elastic modulus is smaller than the first elastic modulus.

3. The endo scope according to claim 2, wherein the portion of the optical member comprises the second transitional surface.

4. The endoscope according to claim 1, wherein the first resin is further disposed on the first transitional surface.

5. The endoscope according to claim 1, wherein the second resin does not contact with the side wall surface.

6. The endoscope according to claim 1, wherein the optical member further includes a distal end surface, the second resin comprises a protruding portion, the protruding portion protrudes 1 µm or more and 100 µm or less from the distal end surface.

7. The endoscope according to claim 1, wherein a gap is formed in at least one of a first space between the first resin and the inner wall surface or a second space between the first resin and the side surface, and the second resin is disposed in the gap.

8. The endoscope according to claim 1, wherein the optical member is one of a lens or a cover glass.

9. The endoscope according to claim 1, wherein the optical member further includes a distal end surface, the barrel further including a distal end face, the distal end surface of the optical member protrudes from the distal end face of the barrel by 10 µm or more and 150 µm or less.

10. The endoscope scope according to claim 1, wherein the first transitional surface comprises a chamfer.

11. An insertion section for use with an endoscope, the insertion section comprising:
    a barrel disposed in a distal end portion of the insertion section, the barrel comprising:
        a through hole disposed in the barrel, the through hole including an inner wall surface; and
        an opening disposed at a distal end of the through hole;
    an optical member disposed in the through hole, the optical member including a proximal end surface, a side wall surface and a first transitional surface, the first transitional surface being disposed between the proximal end surface and the side wall surface;
    a first resin disposed between the inner wall surface and the side surface; and
    a second resin in contact with each of the first resin, a portion of the barrel and a portion of the optical member, the second resin containing light blocking particles.

12. The endoscope according to claim 11, wherein the optical member further includes a distal end surface and a second transitional surface, the second transitional surface being disposed between the side wall surface and the distal end surface, and
    the first resin having a first elastic modulus, the second resin having a second elastic modulus, and the second elastic modulus is smaller than the first elastic modulus.

13. The endoscope according to claim 12, wherein the portion of the optical member comprises the second transitional surface.

14. The endoscope according to claim 11, wherein the first resin is further disposed on the first transitional surface.

15. The endoscope according to claim 11, wherein the second resin does not contact with the side wall surface.

16. The endoscope according to claim 11, wherein the optical member further includes a distal end surface, the second resin comprises a protruding portion, the protruding portion protrudes 1 µm or more and 100 µm or less from the distal end surface.

17. The endoscope according to claim 11, wherein a gap is formed in at least one of a first space between the first resin and the inner wall surface or a second space between the first resin and the side surface, and the second resin is disposed in the gap.

18. The endoscope according to claim 11, wherein the optical member is one of a lens or a cover glass.

19. The endoscope according to claim 11, wherein the optical member further includes a distal end surface, the barrel further including a distal end face, the distal end surface of the optical member protrudes from the distal end face of the barrel by 10 µm or more and 150 µm or less.

20. The endoscope scope according to claim 11, wherein the first transitional surface comprises a chamfer.

* * * * *